United States Patent [19]

Takehara et al.

[11] Patent Number: 5,064,564

[45] Date of Patent: Nov. 12, 1991

[54] OPTICALLY ACTIVE COMPOUND, INTERMEDIATE THEREFOR, PROCESS FOR PRODUCING THE INTERMEDIATE, AND LIQUID-CRYSTAL COMPOSITION

[75] Inventors: Sadao Takehara; Takeshi Kuriyama; Toru Fujisawa, Saitama; Kayoko Nakamura, Chiba; Tamejiro Hiyama; Kusumoto, Tetsuo, both of Kanagawa; Akiko Nakayama, Tokyo, all of Japan

[73] Assignees: Dainippon Ink and Chemicals, Inc.; Sagami Chemical Research Center, both of Tokyo, Japan

[21] Appl. No.: 630,591

[22] Filed: Dec. 20, 1990

[30] Foreign Application Priority Data

Dec. 22, 1989 [JP] Japan .................. 1-331270
Aug. 17, 1990 [JP] Japan .................. 2-216506
Oct. 1, 1990 [JP] Japan .................. 2-263578

[51] Int. Cl.$^5$ ............ C09K 19/34; C07C 227/00; C07C 67/76
[52] U.S. Cl. ............ 25.2/299.61; 252/299.01; 544/298; 544/335; 560/19; 560/38; 560/39; 560/42; 560/102; 560/103; 560/104; 560/106; 560/107; 568/669; 568/704; 568/705; 568/715
[58] Field of Search ............ 252/299.01, 299.61, 252/299.62, 299, 63, 299, 64, 299, 65, 299, 66, 299, 67; 350/350 S, 350 R; 544/298, 315, 318; 558/414, 416, 427, 434; 560/59, 60, 62, 8, 19, 76, 83, 85, 102, 126, 127, 179, 188; 568/669, 704, 705, 715

[56] References Cited

U.S. PATENT DOCUMENTS

| 4,638,073 | 1/1987 | Walba et al. ............ 549/556 |
| 4,777,280 | 10/1988 | Eidman et al. .......... 558/389 |
| 4,880,561 | 11/1989 | Tabohashi et al. ...... 252/299.61 |

FOREIGN PATENT DOCUMENTS

| 3739884.9 | 2/1988 | Fed. Rep. of Germany . |
| 61-243055 | 4/1987 | Japan . |
| 63-190843 | 4/1989 | Japan . |
| 63-119449 | 6/1989 | Japan . |
| 1-146857 | 1/1990 | Japan . |
| 2-000260 | 2/1991 | Japan . |
| 87-24762 | 11/1987 | United Kingdom . |

Primary Examiner—John S. Maples
Assistant Examiner—Wu, Shean C.

Attorney, Agent, or Firm—Armstrong, Nikaido, Marmelstein, Kubovcik & Murray

[57] ABSTRACT

The present invention discloses an optically active compound represented by the following general formula (I):

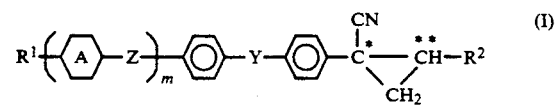

wherein $R^1$ represents an alkyl, alkoxyl, or alkoxyalkanoyloxy group which has 1 to 18 carbon atoms and may be substituted with fluorine, chlorine, or cyano group; $R^2$ represents an alkyl group having 1 to 18 carbon atoms;

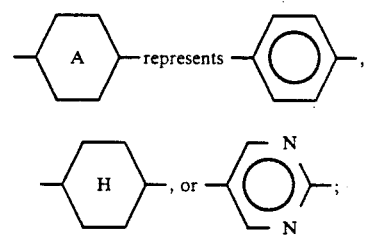

m is 0 or 1; Y represents a single bond, —CH$_2$O—, or —COO—; Z represents a single bond or —COO—; and C* and C** each independently represents an asymmetric carbon atom of the (R) and (S) configuration, an intermediate therefor being represented by the following general formula (II):

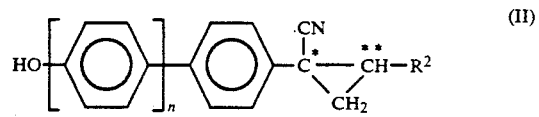

wherein $R^2$ represents an alkyl group having 1 to 18 carbon atoms, n is 0 or 1, and C* and C** each independently represents an asymmetric carbon atom of the (R) or (S) configuration, a process for producing the intermediate, and a liquid-crystal compound using the optically active compound.

11 Claims, No Drawings

OPTICALLY ACTIVE COMPOUND, INTERMEDIATE THEREFOR, PROCESS FOR PRODUCING THE INTERMEDIATE, AND LIQUID-CRYSTAL COMPOSITION

FIELD OF THE INVENTION

The present invention relates to a novel optically active compound, an intermediate therefor, a process for producing the intermediate, and a liquid-crystal composition. More particularly, it relates to a ferroelectric liquid-crystal display material having excellent response and memory characteristics.

BACKGROUND OF THE INVENTION

Liquid-crystal display devices are now used extensively owing to their excellent characteristics (low-voltage operation; small power consumption; thin displays can be constructed; displays can be used in bright light and do not cause the viewer to suffer eyestrain). However, the most commonly used TN type display system is very slow in response compared to light-emitting display systems such as the CRT type and, further, it cannot memorize the information being displayed after the applied electric field is removed (it has no memory effect). Because of these disadvantages, many limitations have been imposed on the applications of the TN type displays to a light shutter that is required to have high-speed response characteristics, a printer head, dynamic pictures that should be driven time-division-wise, such as those in TVs etc. Therefore, the TN type displays are unsuited for these applications Recently, a display system employing a ferro-electric liquid crystal was reported. Since both high-speed response as high as 100 to 1,000 times that of the TN type liquid-crystal display system and memory effect can be obtained with the proposed display system, ferroelectric liquid crystals are expected to be a nextgeneration liquid-crystal display device and studies and developments are currently being made extensively.

The liquid-crystal phases of ferroelectric liquid crystals belong to the chiral smectic phases of the tilt type, but from the practical standpoint, those exhibiting a chiral smectic C (hereinafter referred to as Sc*) phase, which is the lowest in viscosity among the chiral smectic phases, are most preferable.

A large number of liquid-crystal compounds that exhibit an Sc phase have been synthesized and studied. For use as a ferroelectric display device, such liquid-crystal materials are required to: (A) exhibit an Sc* phase over a wide temperature range including room temperature; (B) have a proper phase sequence on the high-temperature side of the Sc* phase, with the helical pitch thereof being large, in order to obtain good orientation; (C) have proper tilt angles; (D) have low viscosities; and (E) show spontaneous polarization that is strong to some degree. However, there is no known liquid-crystal compound which alone satisfies all of these requirements.

Therefore, such a liquid-crystal compound exhibiting an Sc* phase (hereinafter referred to as an Sc* compound) is blended with other Sc* compound(s) etc. and used as a liquid-crystal composition that exhibits an Sc* phase (hereinafter referred to as an Sc* liquid-crystal composition). In any case, an Sc* compound is required to have a low viscosity and to show spontaneous polarization not lower than a certain level, particularly in order to attain high-speed response.

It is also possible to add an optically active compound as a chiral dopant to other liquid-crystal compound or composition that shows a smectic C (hereinafter referred to as Sc) phase and to use the resulting mixture as an Sc* liquid-crystal composition. Since liquid-crystal compositions obtained by this method can have low viscosities, higher-speed response is attainable and, hence, this method is commonly employed. Although the compound to be used as a chiral dopant is not necessarily required to per se exhibit an Sc* phase, compositions containing the compound should have the properties (A) to (E) as specified above with showing an Sc* phase.

Thus, the conventional Sc* compounds have insufficient performances with respect to viscosity, induced spontaneous polarization and helical pitch, etc. and, hence, have failed to provide liquid-crystal materials with good high-speed response characteristics. Therefore, there has been a desire for improvement of such conventional Sc* compounds.

It is known that in order to induce strong spontaneous polarization, the liquid-crystal compound should contain a group with a strong dipole moment at a position that is as close as possible to the core of the liquid-crystal compound molecule and also to an asymmetric carbon. Although carbonyl group is generally known as a group having a strong dipole moment, cyano group can be mentioned as a group having an even stronger dipole moment. However, known as a compound in which a cyano group is directly bonded to an asymmetric carbon are only a compound represented by the formula

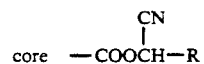

(disclosed in Proceeding for the 12th International Liquid-Crystal Conference and in JP-A-61-243055; the term "JP-A" as used herein means an "unexamined published Japanese patent application") and a compound represented by the formula

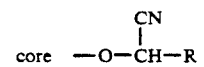

(disclosed in U.S. Pat. No. 4,777,280 and in Walba et al., J. Org. Chem., 54, 4339(1989)), and there have been no known compounds in which a cyano group is located closer to the core.

SUMMARY OF THE INVENTION

For the purpose of eliminating the above-described drawbacks of the conventional Sc* compounds, the present invention has been completed.

Accordingly, an object of the present invention is to provide an optically active compound which, when added as chiral dopant to a base liquid crystal showing an Sc phase or Sc* phase, can induce strong spontaneous polarization and also induce a large helical pitch.

Other objects of the present invention are to provide a ferroelectric liquid-crystal display material which can attain high-speed response and shows excellent orientation characteristics, and further to provide an intermediate for the above optically active compound and a process for producing the intermediate.

DETAILED DESCRIPTION OF THE INVENTION

According to one aspect of the present invention, there is provided an optically active compound represented by the following general formula (I)

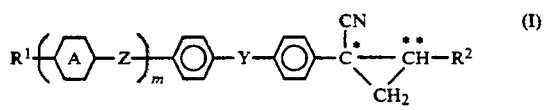

wherein $R^1$ represents an alkyl, alkoxyl, or alkoxyalkanoyloxy group which has 1 to 18, preferably 3 to 12, carbon atoms and may be substituted with fluorine, chlorine, or cyano group; $R^2$ represents an alkyl group having 1 to 18, preferably 1 to 8, carbon atoms;

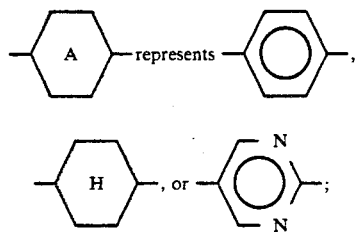

m is 0 or 1; Y represents a single bond, —CH$_2$O—, or —COO—; Z represents a single bond or —COO—; and C* and C** each independently represents an asymmetric carbon atom of the (R) or (S) configuration.

In particular, the optically active compound preferably is represented by general formula (I) in which

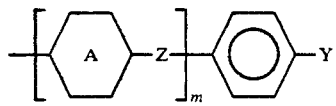

is selected from the group consisting of

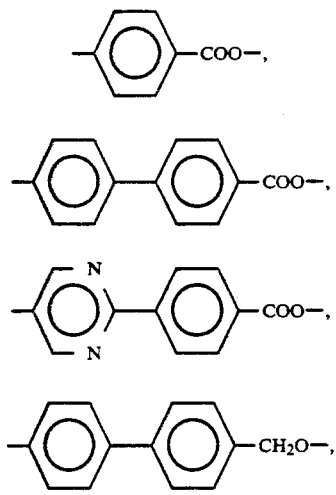

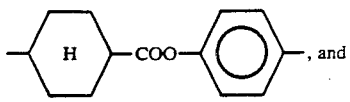

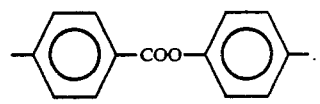

In another aspect of the present invention there is provided a liquid-crystal composition containing the novel optically active compound represented by the above general formula (I).

The liquid-crystal composition according to the present invention contains, as a constituent, at least one compound represented by general formula (I) given above. For use in ferroelectric liquid-crystal display materials in particular, an Sc* liquid-crystal composition is suited in which at least one compound represented by the above general formula (I) has been incorporated as part or all of the chiral dopant in a base liquid crystal that is the main ingredient and exhibits an Sc phase.

The cyano group-containing optically active compound of general formula (I) given above can be produced as follows. In the case where Y in general formula (I) is —COO—, the compound can be easily synthesized by reacting a compound represented by general formula (II)a given below with an acid chloride represented by general formula (VI)a given below in the presence of a base such as pyridine. Alternatively, the optically active compound may be obtained by reacting a compound of general formula (II)a with a carboxylic acid represented by general formula (VII)a given below in the presence of a condensation agent such as dicyclohexylcarbodiimide (DCC). In the case where Y is —CH$_2$O—, the optically active compound can, for example, be produced by reacting a compound of general formula (II)a with a halide represented by general formula (VIII)a given below in the presence of a silver salt such as silver tetrafluoroborate.

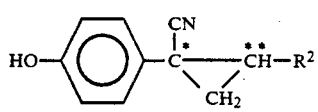 (II)a

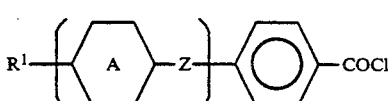 (VI)a

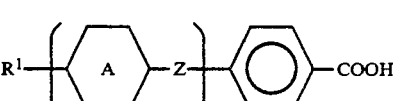 (VII)a

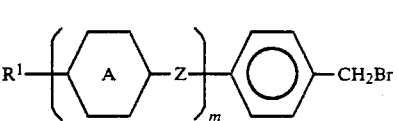 (VIII)a (In the above formulae, $R^1$, $R^2$, m,

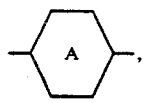

Z, C*, and C** are the same as defined above with reference to general formula (I).)

In the case where Y in general formula (I) is a single bond, the optically active compound can be easily produced by reacting a compound represented by general formula (II)b given below with an acid chloride represented by general formula (VI)b given below in the presence of a base such as pyridine. Alternatively, the optically active compound may be obtained by reacting a compound of general formula (II)b with a carboxylic acid represented by general formula (VII)b given below in the presence of a condensation agent such as dicyclohexylcarbodiimide (DCC).

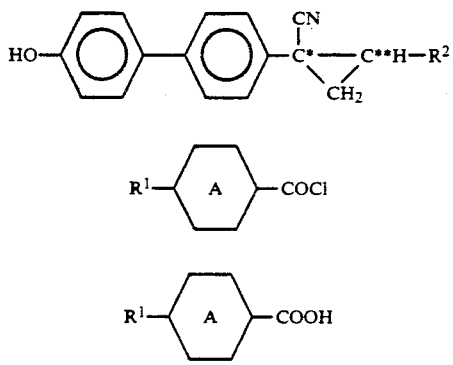

(In the above formulae, $R^1$, $R^2$,

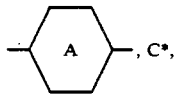

and C** are the same as defined above with reference to general formula (I).)

The phenol derivative of general formula (II), which is an optically active compound having a cyano group, also is a novel compound. This compound and a process for the production thereof are also provided by the present invention.

The compounds of general formulae (II)a and (II)b can be produced as follows.

First, 4-methoxyphenylacetonitrile or 4-(4-methoxyphenyl)phenylacetonitrile is reacted with an optically active epoxide represented by general formula (III) in the presence of a strong base such as butyllithium or lithium diisopropylamide (LDA), thereby to obtain a compound represented by general formula (IV).

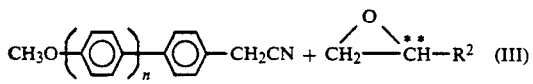

| strong base (e.g., butyllithium, LDA, etc.)

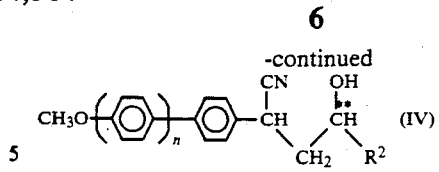

Although the compound of general formula (IV) is obtained in the form of a diastereomeric mixture, the isomers can be separated from each other by ordinary separation techniques such as, for example, silica gel column chromatography.

Each isomer obtained is then tosylated at the OH group by use of p-toluenesulfonyl chloride in the presence of pyridine. The resulting tosyl group-containing compound is reacted with a strong base to obtain a compound represented by general formula (V) given below.

The compound of general formula (V) is then subjected to demethylation in which the methyl group is reacted with, for example, aluminum chloride-dimethyl sulfide, thereby obtaining a compound of general formula

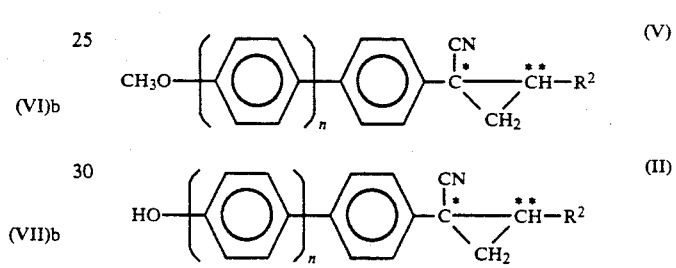

(In above formulae, n is 0 or 1, and $R^2$, C*, and C** are the same as defined above with reference to general formula (I).)

The compounds of general formulae (VI)a, (VI)b, (VII)a, and (VII)b are mostly already known, and may be obtained by ordinary synthesizing techniques. The compounds of general formula (VIII)a may alternatively be obtained by reducing the compound of general formula (VI)a or (VI)b and then brominating the reduced compound.

The optically active compound of general formula (I) according to the present invention can be obtained as described above. Specific compounds which belong to such compound of general formula (I) and intermediates for the optically active compound which are represented by general formula (II) can be identified by means of measurement of melting point and other phase transition temperatures, infrared spectrophotometry (IR), nuclear magnetic resonance spectroscopy (NMR), mass spectrometry (MS), etc.

Examples of the compound of general formula (I) which were obtained by the above-described methods are listed in Table 1 given later.

One of the excellent features of the compound of general formula (I) is that it induces a sufficiently large spontaneous polarization ($P_s$).

For example, an Sc* liquid-crystal composition consisting of 10% by weight (hereinafter all percents are by weight) of the compound obtained in Example 14 given later and 90% of a base liquid crystal showing an Sc phase and an Sc* liquid-crystal composition consisting of 10% of the compound obtained in Example 24 given later and 90% of the same base liquid crystal have Ps values as large as 13.8 and 9.1 nC/cm², respectively, at 25° C. These values are found to be very large in view of the fact that Sc* compounds derived from (S)-2-methylbutanol, such as, for example, (S)-2-methylbutyl p-decyloxybenzylideneaminobenzoate (DOBAMBC), which are the most commonly used asymmetric sources for liquid crystals, have Ps values of about 4 nC/cm² even when used alone. The reason for such large Ps values for the compounds of this invention may be that the asymmetric center of the compound of general formula (I) is directly bonded to the core of the liquid-crystal compound molecule and also to the cyano group which has a strong dipole moment, and that the free rotation about the molecule axis is inhibited by the cyclohexane ring on the adjacent asymmetric carbon. Particularly in the case where an asymmetric carbon is present in R¹, the chiral groups at both sides are thought to produce a considerable synergistic effect. Therefore, by incorporating the compound of general formula (I) as a chiral dopant into a nonchiral compound or nonchiral liquid-crystal composition in an amount of about 1 to 2% or more, a spontaneous polarization sufficient for high-speed response can be induced.

The compound of general formula (I) according to the present invention has another advantage that by suitably selecting the absolute configuration of each asymmetric carbon, the compound can be made to induce a very large helical pitch.

For example, an Sc* liquid-crystal composition consisting of 10% of the compound of Example 21 given later and 90% of a base liquid crystal showing an Sc phase and an Sc* liquid-crystal composition consisting of 10% of the compound of Example 24 given later and 90% of the same base liquid crystal show, in their N* phase state, helical pitches that are too large to measure. Such large helical pitches eliminate the necessity of the troublesome helical pitch adjustment. Thus, an Sc* composition with good orientation characteristics can be obtained only by incorporating the optically active compound of this invention into a base liquid crystal.

The compound of general formula (I) according to the present invention is suited rather for use as a dopant to give a liquid-crystal composition than for use alone. In the case of formulating such a liquid-crystal composition, a chiral dopant consisting of at least one optically active compound of general formula (I) and, according to need, other optically active compound(s) is added to other liquid-crystal compound or composition. In particular, in order to formulate a liquid-crystal composition for use as a ferroelectric liquid-crystal display device, it is desirable that the optically active compound of this invention be added as a chiral dopant to a base liquid-crystal compound or composition which shows an Sc phase but is not chiral. The reason for this is that since the optically active compound of general formula (I) has the property of inducing a sufficiently large spontaneous polarization as described above, incorporation of 1 to 2% or more of the optically active compound into an Sc liquid crystal enables the resulting composition to show a certain degree of induced spontaneous polarization and to attain high-speed response. Even if the compound of general formula (I) per se does not show an Sc* phase, incorporation thereof never narrows the range of temperatures at which the liquid-crystal composition exhibits an Sc* phase.

Furthermore, the compound of general formula (I) can be incorporated into nematic liquid crystals in a small quantity to prevent the TN liquid crystals from suffering so-called reverse domain, and it can also be used as an STN liquid crystal, etc.

Examples of Sc compounds to which the optically active compound of general formula (I) according to the present invention can be added as a chiral dopant to prepare Sc liquid-crystal compositions include phenyl benzoate-type compounds represented by the following general formula (A) and pyrimidine-type compounds represented by the following general formula (B):

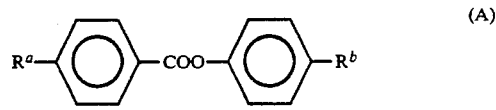

wherein $R^a$ and $R^b$ are identical or different and independently represent a straight-chain or branched alkyl, alkoxyl, alkoxycarbonyl, alkanoyloxy, or alkoxycarbonyloxy group;

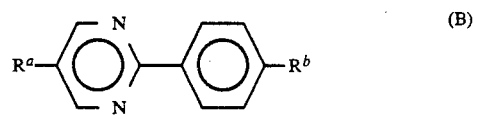

wherein $R^a$ and $R^b$ are the same as those in general formula (A) above.

Further, compounds represented by the following general formula (C), which includes general formulae (A) and (B), may be used for the same purpose:

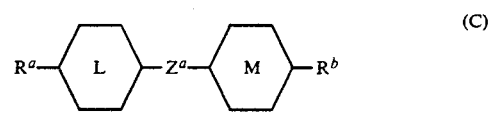

wherein $R^a$ and $R^b$ are the same as those in general formula (A);

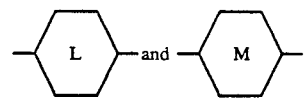

are identical or different and independently represent

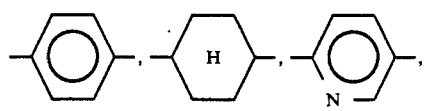

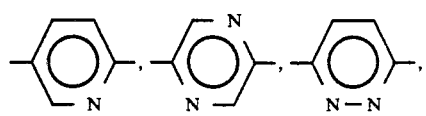

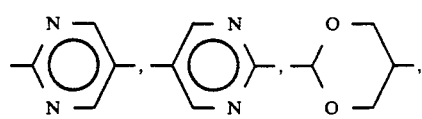

-continued

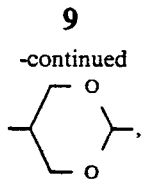

or halogen-substituted groups derived therefrom; and $Z^a$ represents —COO—, —OCO—, —CH$_2$O—, —OCH$_2$—, —CH$_2$CH$_2$—, —C≡C—, or a single bond.

For the purpose of widening the Sc-phase temperature range into a high-temperature region, three-ring compounds represented by general formula (D) may be used:

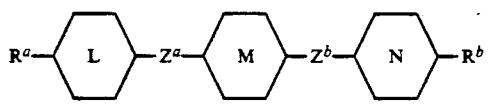 (D)

wherein $R^a$ and $R^b$ are the same as those in general formula (A);

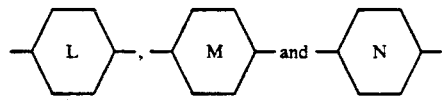

are identical or different and are the same as

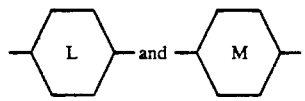

in general formula (C) above; and $Z^a$ and $Z^b$ are identical or different and are the same as $Z^a$ in general formula (C) above.

It is effective to use these compounds in the form of an Sc liquid-crystal composition obtained by mixing such compounds. Each of the compounds constituting such a composition is not necessarily required to exhibit an Sc phase as long as the resulting composition shows an Sc phase.

By incorporating as chiral dopant the compound of this invention represented by general formula (I) and, if needed, other optically active compounds into the Sc liquid-crystal composition obtained above, a liquid-crystal composition that exhibits an Sc* phase over a wide temperature range including room temperature can be easily obtained.

The liquid-crystal composition, obtained by incorporating the optically active compound of general formula (I) according to the present invention into an Sc compound or Sc liquid-crystal composition, may be sandwiched between two transparent glass electrodes in such a manner that the composition is enclosed in the form of a thin film about 1 to 20 μm thick. This construction can be used as a display cell, but in order to obtain good contrast, the cell should be of a monodomain structure in which orientation is uniform. Many attempts have so far been made to obtain such monodomain cells. In order for a liquid-crystal material to have good orientation characteristics, the liquid-crystal material is required to show a phase sequence of (I)-(N*)-(S$_A$)-(Sc*), and to have elongated helical pitches in the N* phase and Sc* phase. Although an increased helical pitch can be obtained by blending suitable amounts of chiral compounds having opposite twist directions, this preparation of a chiral dopant can be made easy with the optically active compound of general formula (I) according to the present invention because the compound of general formula (I) induces a sufficiently large helical pitch especially in an N*-phase temperature range, as described above.

In the optically active compound represented by general formula (I) according to the present invention, at least two asymmetric carbons (C* and C**) are present.

The absolute configuration of C depends on that of the optically active epoxide which is represented by general formula (III) and was used as a raw material to synthesize the compound of general formula (I). If the absolute configuration in the epoxide was (R), that of C is (S). If the absolute configuration of the epoxide was (S), that of C** is (R).

With respect to the absolute configuration of C*, it can be both (R) and (S). However, either of the isomers can be selectively produced by the separation of isomers in the stage of intermediates.

The polarity of the spontaneous polarization induced by the optically active compound of general formula (I) according to the present invention depends on the absolute configuration of the asymmetric carbon C*, in the case where the composition does not contain asymmetric carbons other than those of the compound of general formula (I). That is, C* of the (R) configuration results in the polarity of ⊕, while (S) configuration results in ⊖.

On the other hand, the direction of the helical pitch induced in an N* phase depends on C** rather than C* That is, C** of the (S) configuration results in "left", while (R) configuration results in "right". Therefore, by suitably selecting a combination of the absolute configurations of C* and C** (a compound of general formula (I) with any combination of C* and C** configurations can be synthesized), there can be obtained any of the combinations, (left, ⊕), (left, ⊖), (right, ⊕), and (right, ⊖).

The above is a great advantage in preparing a chiral dopant. Even when the compound of general formula (I) is combined with any other optically active compound, the helical pitch can be elongated without causing the induced spontaneous polarizations to weaken each other. Further, even by use of the compound of general formula (I) alone, helical pitch can be easily adjusted without impairing induced spontaneous polarization.

The present invention will be explained below in more detail by reference to the following Examples, which should not, of course, be construed to be limiting the spirit and scope of the invention.

In the Examples, the structures of compounds were determined by nuclear magnetic resonance spectroscopy (NMR), infrared spectrophotometry (IR), and mass spectrometry (MS). Phase transition temperatures were measured by means of both a polarizing microscope equipped with a temperature-regulating stage and a differential scanning calorimeter (DSC). In the IR data, (KBr) indicates measurement on formed tablets, (neat) indicates measurement on liquid films, and (Nujol) indicates measurement on suspensions in liquid paraffin. In the NMR data, (CDCl$_3$) and (CCl$_4$) indicate solvents, while "s" means a singlet, "d" a doublet, "t" a triplet, "q" a quartet, and "m" a multiplet. Further, "broad" means a broad absorption, and "J" indicates the coupling constant. In the MS data, "M+" indicates a parent peak and the values in parentheses show the relative intensities for respective peaks. Temperature values are given in terms of °C. All percentages indicating compositions are shown by weight.

EXAMPLE 1

Synthesis of (2S,4R)-4-p-toluenesulfonyloxy-2-(4-methoxyphenyl)-decanenitrile (1-a)

Synthesis of (2S,4R)- and (2R,4R)-4-hydroxy-2-(4-methoxyphenyl)decanenitriles:

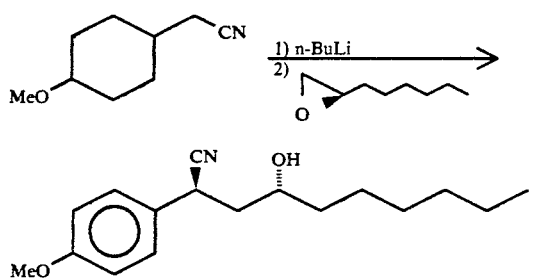

To a solution of 750 mg of 4-methoxyphenylacetonitrile in 10 ml of tetrahydrofuran (THF) was added 3.3 ml of a 1.55 M hexane solution of butyllithium (n-BuLi) at −78° C. This mixture was stirred for 1 hour, and then a solution of 651 mg of (2R)-1,2-epoxyoctane in 5 ml of THF was added. The temperature of the resulting mixture was raised to −10° C. A saturated aqueous solution of ammonium chloride was then added, and the resulting mixture was subjected to extraction with ether, followed by column chromatography (Kieselgel 60, hexane/ethyl acetate=4/1), thereby obtaining 926 mg (yield 70%) of an about 1:1 mixture of (2S,4R)- and (2R,4R)-4-hydroxy-2-(4-methoxyphenyl)decanenitriles. The two products were separated by means of medium-pressure column chromatography.

Identification data for the (2S,4R)-4-hydroxy-2-(4-methoxyphenyl)decanenitrile are as follows.

Oily substance, $R_f$ 0.29 (hexane/ethyl acetate=3/1)

$[\alpha]_D^{20}$ −29.5° (c=2.61, MeOH)

IR (neat) 3450, 2240, 1610, 1510, 1250, 1175, 1030, 825, 625 cm$^{-1}$ $^1$H NMR (CDCl$_3$) δ 0.88 (t, J=7.0 Hz, 3H) 1.22–1.54 (m, 10H), 1.65 (broad s, 1H), 1.80 (ddd, J=13.9, 10.5, 4.4 Hz, 1H), 1.98 (ddd, J=13.9, 11.5, 2.4 Hz, 1H), 3.39 (m, 1H), 3.81 (s, 3H), 4.01 (dd, J=11.5, 4.4 Hz, 1H, 6.90 (d, J=8.7 Hz, 2H), 7.27 (d, J=8.7 Hz, 2H)

MS m/z: 275 (M+, 3.0), 15.9 (100)

Elementary analysis: Calculated for C$_{17}$H$_{25}$NO$_2$: C, 74.14; H, 9.15; N, 5.09%. Found: C, 73.84; H, 9.02; N, 4.81%

Identification data for the (2R,4R)-4-hydroxy-2-(4-methoxyphenyl)decanenitrile are as follows.

Oily substance, $R_f$ 0.24 (hexane/ethyl acetate=3/1)

$[\alpha]_D^{20}$ −20.8° (c=2.06, MeOH)

IR (neat) 3450, 2240, 1610, 1510, 1250, 1030, 825, 625 cm$^{-1}$ $^1$H NMR (CDCl$_3$) δ 0.86 (t, J=6.8 Hz, 3H), 1.18–1.48 (m, 10H), 1.50 (broad, s, 1H), 1.96 (ddd, J=13.8, 9.9, 3.2 Hz, 1H), 2.08 (ddd, J=13.8, 9.7, 5.3 Hz, 1H), 3.39 (m, 1H), 3.81 (s, 3H), 4.01 (dd, J=9.9, 5.3 Hz, 1H), 6.90 (d, J=8.7 Hz, 2H), 7.26 (d, J=8.7 Hz, 2H)

MS m/z: 275 (M+, 4.0), 159 (100)

Elementary analysis: Calculated for C$_{17}$H$_{25}$NO$_2$: C, 74.14; H, 9.15; N, 5.09%. Found: C, 73.80; H, 9.24, N, 4.92%

(1-b)

Synthesis of (2S,4R)-4-p-toluenesulfonyloxy-2-(4-methoxyphenyl)decanenitrile:

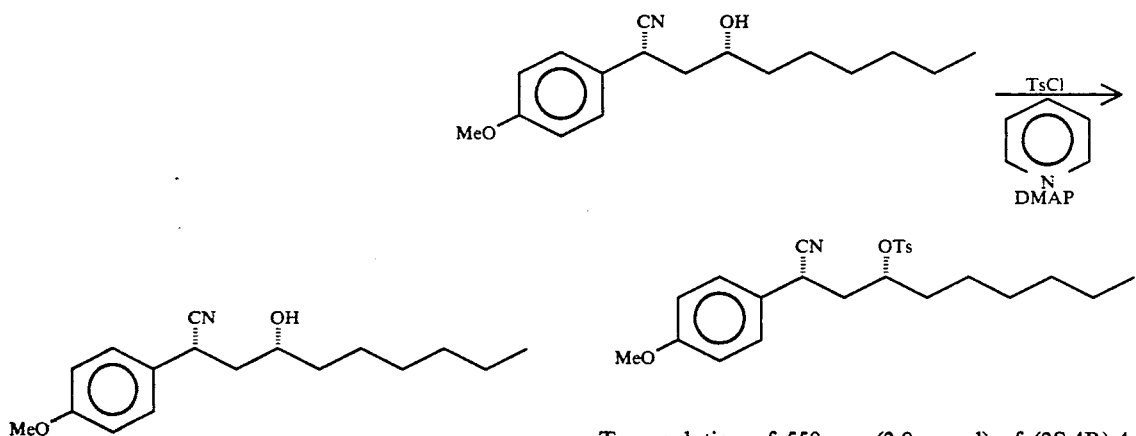

To a solution of 559 mg (2.0 mmol) of (2S,4R)-4-hydroxy-2-(4-methoxyphenyl)decanenitrile in 5 ml of pyridine were added, with cooling with ice, a solution of 774 mg (4.1 mmol) of p-toluenesulfonyl chloride (TsCl) in 3 ml of pyridine and 24 mg (0.2 mmol) of 4-(N,N-dimethylamino)pyridine (DMAP). This mixture was stirred at room temperature for 3 days. The pH of the reaction mixture was adjusted to 7 with diluted hydrochloric acid, and this reaction mixture was subjected to extraction with ether (150 ml). The resulting ether solution was washed with diluted hydrochloric acid and saturated sodium chloride aqueous solution, and then concentrated. The residue was separated and purified by column chromatography (Kieselgel 60, hexane/ethyl acetate=4/1), thereby obtaining 550 mg (yield 63%) of (2S,4R)-4-p-toluenesulfonyloxy-2-(4-methoxyphenyl)-decanenitrile.

Identification data are given below.

Oily substance $[\alpha]_D^{20}$ +14° (c=1.1, MeOH)

IR (neat) 2940, 2860, 2240, 1650, 1600, 1510, 1460, 1360, 1250, 1170, 1030, 895 cm$^{-1}$ $^1$H NMR (CDCl$_3$) δ 0.85 (t, J=7.0 Hz, 3H), 1.19 (m, 8H), 1.64 (m, 2H), 2.07 (m, 2H), 2.46 (s, 3H), 3.70 (m, 1H), 3.80 (s, 3H), 4.72 (m, 1H), 6.88 (d, J=8.7 Hz, 2H), 7.18 (d, J=8.7 Hz, 2H), 7.37 (d, J=8.3 Hz, 2H), 7.85 (d, J=8.3 Hz, 2H).

MS m/z: 429 (M+, 0.8), 258 (56.2), 257 (100).

Elementary analysis: Calculated for C$_{24}$H$_{31}$NO$_4$S: C, 67.10; H, 7.27; N, 3.26; S, 7.46%. Found: C, 67.17; H, 7.43; N, 3.14; S, 7.52%

EXAMPLE 2

Synthesis of (2R,4R)-4-p-toluenesulfonyloxy-2-(4-methoxyphenyl)-decanenitrile

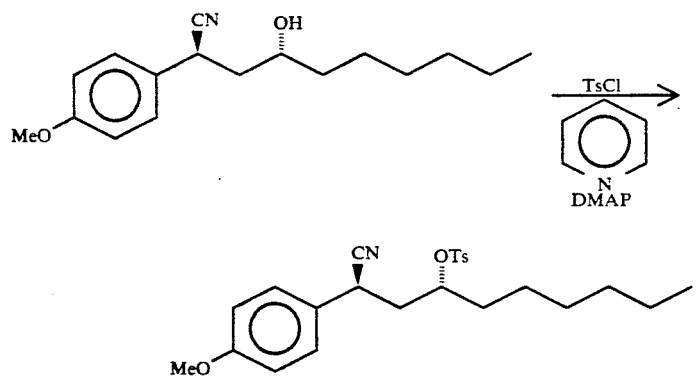

From 730 mg (2.65 mmol) of (2R,4R)-4-hydroxy-2(4-methoxyphenyl)decanenitrile as obtained in Example 1-a, 563 mg (yield 50%) of (2R,4R)-4-p-toluenesulfonyloxy-2-(4-methoxyphenyl)decanenitrile was obtained in the same manner as in Example 1-b.

Identification data are given below.

Oily substance

[α]$_D^{20}$ +5.7° (c=1.1, CHCl$_3$)

IR (neat) 2930, 2870, 2240, 1610, 1600, 1360, 1250, 890 cm$^{-1}$ $^1$H NMR (CDCl$_3$) δ 0.83 (t, J=7.0 Hz, 3H), 1.05–1.22 (m, 8H), 1.54–1.60 (m, 2H), 2.10 (ddd, J=14.6, 8.6, 4.1 Hz, 1H), 2.36 (ddd, J=14.6, 7.5, 6.2 Hz, 1H), 2.46 (s, 3H), 3.82 (s, 3H), 3.87 (dd, J=8.6, 6.2 Hz, 1H), 4.49 (dtd, J=7.5, 6.0, 4.1 Hz, 1H), 6.90 (d, J=8.8 Hz, 2H), 7.23 (d, J=8.8 Hz, 2H), 7.35 (d, J=8.3 Hz, 2H), 7.79 (d, J=8.3 Hz, 2H).

MS m/z: 429 (M+, 1), 258 (45), 257 (100), 231 (15), 159 (68)

Elementary analysis: Calculated for C$_{24}$H$_{31}$NO$_4$S: C, 67.10; H, 7.27; N, 3.26; S, 7.46%. Found: C, 66.90; H, 7.33; N, 3.19; S, 7.60%

EXAMPLE 3

Synthesis of (1R,2S)- and (1S,2S)-1cyano-2-hexyl-1-(4-methoxyphenyl)cyclopropanes

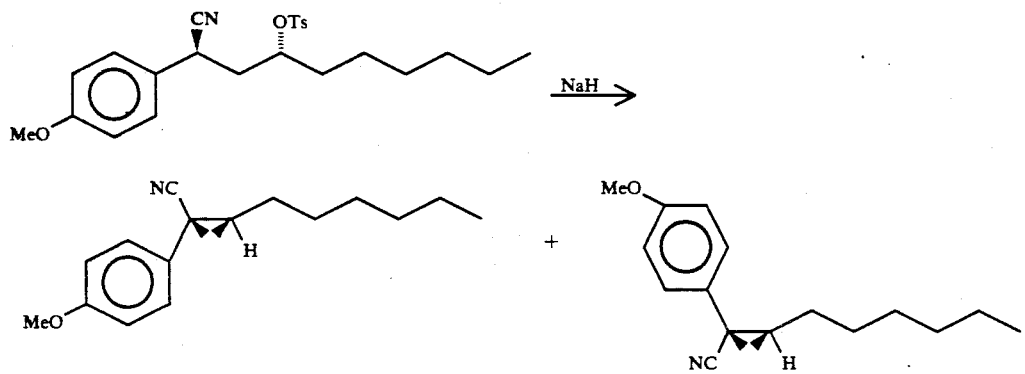

To a dispersion of 18 mg (0.75 mmol) of sodium hydride in 10 ml of DMF was added, with cooling with ice, a solution of 300 mg (0.70 mmol) of (2S,4R)-4-p-toluenesulfonyloxy-2-(4-methoxyphenyl)-decanenitrile in 10 ml of DMF. The resulting mixture was stirred at room temperature for 2 hours. The reaction mixture was neutralized by adjusting the pH thereof to 7 with diluted hydrochloric acid, and then subjected to extraction with 250 ml of ether. The resulting ether solution was washed with water, dried with anhydrous magnesium sulfate, and then concentrated. The isomers in the residue were separated by silica gel column chromatography (Kieselgel 60, hexane/ethyl acetate=9/1) and then further separated and purified by high-pressure liquid chromatography for separation (Tosoh Corporation, Japan; Silica-60, 21.5 mmID×300 mm, hexane/ethanol=100/1). Thus, 163 mg (yield 90%, optical purity 94% ee) of a nonpolar product, (1R,2S)-1-cyano-2-hexyl-1-(4-methoxyphenyl)cyclopropane and 7 mg (yield 4%) of a polar product, (1S,2S)-1-cyano-2-hexyl-1-(4-methoxyphenyl)cyclopropane, were obtained.

Identification data for the (1R,2S)-1-cyano-2-hexyl-1-(4-methoxyphenyl)cyclopropane are as follows.

Oily substance

[α]$_D^{20}$ +37.0° (c=1.2, CHCl$_3$)

IR (neat) 2950, 2875, 2245, 1515, 1250, 1035 cm$^{-1}$ $^1$H NMR (CDCl$_3$) δ 0.89 (t, J=6.9 Hz, 3H), 1.29–1.60 (m, 11H), 1.67–1.73 (m, 2H), 3.80 (s, 3H), 6.86 (d, J=8.8 Hz, 2H), 7.20 (d, J=8.8 Hz, 2H)

$^{13}$C NMR (CDCl$_3$) δ 14.0 (q, J=124.3 Hz), 19.2 (m), 22.5 (t, m, J=125.3 Hz), 23.4 (tm, J=163.5 Hz), 28.7 (tm, J=120.7 Hz), 28.9 (tm, J=124.4 Hz), 31.6 (tm, J=124.4 Hz), 55.2 (q, J=143.9 Hz) 114.1 (dd, J=159.7, 5.0 Hz), 121.3 (tt, J=32.9 Hz), 127.3 (dd, J=157.3, 7.3 Hz), 128.7 (m), 158.8 (m).

MS m/z: 257 (M$^+$, 14), 172 (11), 97 (12), 96 (100)
High-resolution MS: M$^+$
Calculated for C$_{17}$H$_{23}$ON: 257.1774. Found 257.1790
Identification data for the (1S,2S)-1-cyano-2-hexyl-1-(4-methoxyphenyl)cyclopropane are as follows.
Oily substance
[α]$_D^{20}$ +27.8° (c=1.2, CHCl$_3$)
IR (neat) 2940, 2870, 2240, 1515, 1460, 1295, 1250, 1180, 1030, 830 cm$^{-1}$
$^1$H NMR (CDCl$_3$) δ 0.72–0.81 (m, 1H), 0.84 (t, J=7.2 Hz, 3H), 1.13–1.32 (m, 10H), 1.66 (dd, J=9.1, 5.3 Hz, 1H), 1.71–1.78 (m, 1H), 3.81 (s, 3H), 6.88 (d, J=8.8 Hz, 2H), 7.25 (d, J=8.8 Hz, 2H).
MS m/z: 257 (M$^+$, 8), 120 (11), 111 (11), 110 (100)
High-resolution MS: M$^+$
Calculated for C$_{17}$H$_{23}$ON; 257.1774. Found: 257.1775

EXAMPLES 4 TO 10

(2S,4R)- and (2R,4R)-4-p-Toluenesulfonyl-2-(4-methoxyphenyl)decanenitriles were reacted with bases such as sodium hydride, potassium t-butoxide, and lithium diisopropylamide (LDA), thereby synthesizing (1R,2S)- and (1S,2S)-1-cyano-2-hexyl-1-(4-methoxyphenyl)cyclopropanes. The results obtained are summarized in Table 1 below.

TABLE 1

| Example | 4-p-Toluenesulfonyloxy-2-(4-methoxyphenyl)decanenitrile | Base | Solvent | Yield (%) | NC (1R, 2S:1S, 2S) |
|---|---|---|---|---|---|
| 4 | (2S, 4R) | NaH | DMSO | 73 | (10:1) |
| 5 | (2R, 4R) | " | DMF | 94 | (10:1) |
| 6 | (2S, 4R) | t-BuOK | DMF | 91 | (1:1) |
| 7 | " | " | C$_6$H$_6$ | 80 | (4:5) |
| 8 | " | " | THF | 74 | (5:3) |
| 9 | (2R, 4R) | " | DMF | 87 | (10:1) |
| 10 | (2S, 4R) | LDA | THF | 40 | (5:3) |

EXAMPLE 11

Synthesis of (1R,2S)-1-cyano-2-hexyl-1-(4-hydroxyphenyl)cyclopropane

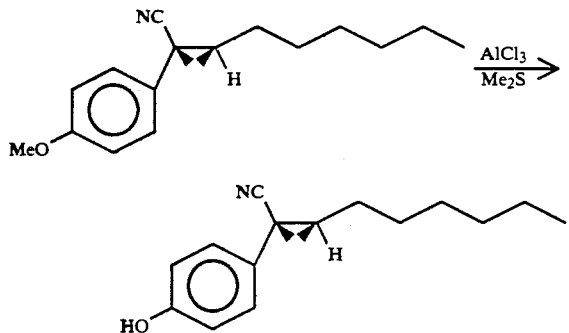

To a solution of 1.38 g (10.4 mmol) of aluminum chloride in 10 ml of dimethyl sulfide (Me$_2$S) was added, with cooling with ice, a solution of 267 mg (1 mmol) of (1R,2S)-1-cyano-2-hexyl-1-(4-methoxyphenyl)cyclopropane in 10 ml of dichloromethane. This mixture was stirred with heating for 30 minutes. Saturated sodium hydrogen carbonate aqueous solution was added to the reaction mixture, and the mixture was then subjected to extraction with 250 ml of ethyl acetate. The resulting ethyl acetate solution was washed with saturated sodium chloride aqueous solution, dried with anhydrous magnesium sulfate, and then concentrated. The residue was separated and purified by column chromatography (Kieselgel 60, hexane/ethyl acetate=5/1), thereby obtaining 197 mg (yield 81%) of (1R,2S)-1-cyano-2-hexyl-1-(4-hydroxyphenyl)cyclopropane.
Identification data are given below.
Oily substance [α]$_D^{20}$ +38° (c=0.94, CHCl$_3$)
IR (neat) 3400, 2930, 2860, 2230, 1650, 1510, 1435, 1245, 830 cm$^{-1}$
$^1$H NMR (CDCl$_3$) δ 0.89 (t, J=6.9 Hz, 3H), 1.28–1.61 (m, 11H), 1.65–1.71 (m, 2H), 6.25 (broad s, 1H), 6.80 (d, J=8.7 Hz, 2H), 7.12 (d, J=8.7 Hz, 2H)
MS m/z: 243 (M$^+$, 8), 146 (12), 145 (100)
High-resolution MS: M$^+$
Calculated for C$_{16}$G$_{21}$ON: 243.1618. Found: 243.1613

EXAMPLE 12

Synthesis of (1S,2S)-1-cyano-2-hexyl-1-(4-hydroxyphenyl)cyclopropane

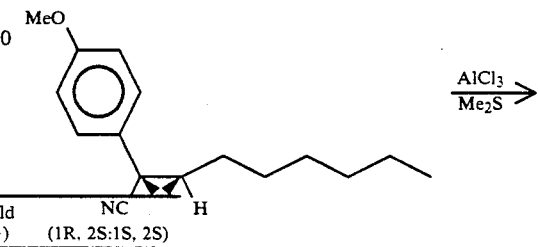

From 308 mg (1.20 mmol) of 1S,2S)-1-cyano-2-hexyl-1-(4methoxyphenyl)cyclopropane, 238 mg (yield 82%) of a polar product, (1S,2S)-1-cyano-2-hexyl-1-(4-hydroxyphenyl)cyclopropane, was obtained under the same conditions as in Example 11.
Identification data are given below.
Oily substance
[α]$_D^{20}$ +32° (c=0.96, CHCl$_3$)
IR (neat) 3400, 2940, 2875, 2240, 1610, 1595, 1510, 1435, 1270, 1220, 1170, 835 cm$^{-1}$ $^1$H NMR (CDCl$_3$) δ 0.72–0.82 (m, 1H), 0.83 (t, J=7.2 Hz, 3H), 1.13–1.32 (m, 10H), 1.65 (dd, J=9.2, 5.3 Hz, 1H), 1.70–1.78 (m, 1H), 4.20–5.60 (broad, s, 1H), 6.71 (d, J=8.7 Hz, 2H), 7.20 (d, J=8.7 Hz, 2H)

MS m/z: 243 (M+, 7), 146 (12), 145 (100)
High-resolution MS: M+
Calculated for C$_{16}$H$_{21}$ON: 243.1618. Found: 243.1614

EXAMPLE 13

Synthesis of a compound of general formula (II)b (13-a)

Synthesis of ethyl 4-(4-methoxyphenyl)phenylacetate:

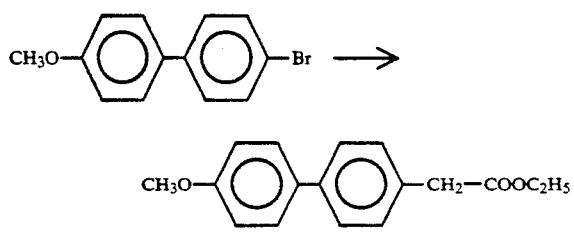

A solution of 2.6 g (4.0 mmol) of dichlorobis(triphenylphosphine) nickel and 2.1 g (8.0 mmol) of triphenylphosphine in 30 ml of ether was cooled to 0° C. in an argon atmosphere. To this solution, 1.8 M ethylmagnesium bromide solution in ether was added in an amount of 4.4 ml (8.0 mmol). The resulting mixture was stirred for 1 hour, and the solvent was then removed by evaporation under reduced pressure. To the residue was added a solution of 4.3 g (16.4 mmol) of 4-bromo-4'-methoxybiphenyl in 20 ml of tetrahydrofuran (THF) and 30 ml of dimethoxymethane, and was also added 10 ml of hexamethylphosphoric triamide (HMPA). Thereto was added at 0° C. a Reformatsky reagent prepared from 10.0 g (60.0 mmol) of ethyl bromoacetate, 6.5 g (100 mmol) of zinc, and 10 ml of dimethoxymethane. The resulting mixture was stirred at room temperature overnight. Thereafter, 50 ml of 3 M hydrochloric acid was added thereto, and this mixture was subjected to extraction with 250 ml of ether. The resulting ether solution was washed with purified water, and then concentrated under reduced pressure. The residue was separated and purified by column chromatography (hexane/ethyl acetate=5/1), thereby obtaining 2.16 g (yield 51%) of ethyl 4-(4-methoxyphenyl)phenylacetate.

Colorless plates, Melting point 68° C.
IR (KBr) 3000, 2930, 1740, 1615, 1510, 1375, 1280, 1260, 1210, 1185, 1040, 820, 800, 500 cm$^{-1}$ $^1$H NMR (CDCl$_3$) δ 1.26 (t, J=7.1 Hz, 1H), 3.63 (s, 2H), 3.84 (s, 3H), 4.16 (q, J=7.1 Hz, 2H), 6.96 (d, J=8.8 Hz, 2H), 7.34 (d, J=8.1 Hz, 2H), 7.50 (d, J=8.3 Hz, 2H), 7.51 (d, J=8.8 Hz, 2H)

MS m/z: 270 (M+, 78), 198 (16), 197 (100) 154 (17)
Elementary analysis: Calculated for C$_{17}$H$_{18}$O$_3$: C, 75.53; H, 6.71% Found: C, 75.63; H, 6.76%

(13-b)

Synthesis of 4-(4-methoxyphenyl)phenylacetic acid:

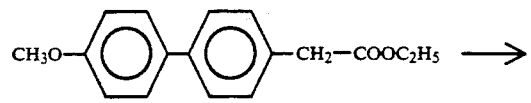

-continued

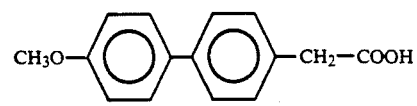

To a solution of 250 mg (0.93 mmol) of ethyl 4-(4-methoxyphenyl)phenylacetate in 30 ml of ethanol was added, with cooling with ice, 5 ml of 40% sodium hydroxide aqueous solution. This mixture was stirred at room temperature for 2 days. The reaction mixture was neutralized with 3 M hydrochloric acid, and the solvent was then removed by evaporation under reduced pressure. Thereafter, the pH of the resulting mixture was adjusted to 1 with 3 M hydrochloric acid, and this mixture was subjected to extraction with 200 ml of ether. The resulting ether solution was washed with saturated sodium chloride aqueous solution, dried with anhydrous magnesium sulfate, filtered, and then concentrated. Thus, 524 mg (yield 94%) of 4-(4-methoxyphenyl)-phenylacetic acid was obtained.

Colorless plates, Melting point 186°–188° C.
IR (KBr) 3050, 2950, 1725, 1695, 1610, 1505, 1420, 1295, 1275, 1210, 1180, 1135, 815, 660 cm$^{-1}$ $^1$H NMR (CDCl$_3$) δ 3.62 (s, 2H), 3.82 (s, 3H), 6.97 (d, J=8.9 Hz, 2H), 7.32 (d, J=8.3 Hz, 2H), 7.52 (d, J=8.3 Hz, 2H), 7.53 (d, J=8.9 Hz, 2H), MS m/z: 242 (M+, 100), 198 (13), 197 (84), 154 (16)
Elementary analysis: Calculated for C$_{15}$H$_{14}$O$_3$: C, 73.36; H, 5 83% Found: C, 74.43; H, 5.81%

(13-c)

Synthesis of 4-(4-methoxyphenyl)phenylacetonitrile:

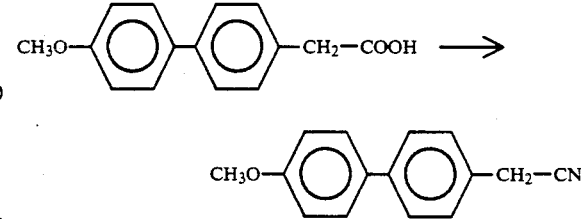

A solution of 1.0 g (5.4 mmol) of 4-(4-methoxyphenylphenylacetic acid in 20 ml of chloroform solution of ethyl polyphosphate (PPE) was stirred for 2 hours under an ammonia atmosphere at room temperature. Thereto was added 10 ml of PPE, and the resulting mixture was heated to reflux for 2 hours under an argon atmosphere. Saturated sodium carbonate aqueous solution was added to neutralize the reaction mixture, and the mixture was then subjected to extraction with 250 ml of ether. The resulting ether solution was washed with saturated sodium chloride aqueous solution, and then concentrated under reduced pressure. The residue was separated and purified by column chromatography (hexane/ethyl acetate=3/1), thereby obtaining 809 mg (yield 67%) of 4-(4-methoxy-phenyl)phenylacetonitrile.

Colorless crystals, Melting point 129°–130° C.
IR (KBr)2250, 1615, 1505, 1410, 1285, 1260, 1180, 1040, 805 cm$^{-1}$ $^1$H NMR (CDCl$_3$) δ 3.78 (s, 2H), 3.85 (d, 3H), 6.98 (d, J=8.8 Hz, 2H), 7.37 (d, J=8.4 Hz, 2H), 7.51 (d, J=8.8 Hz, 2H), 7.56 (d, J=8.4 Hz, 2H), MS m/z: 223 (M+, 100), 208 (19), 180 (30), 152 (15), 139 (12)

Elementary analysis: Calculated for C$_{15}$H$_{13}$NO: C, 80.69; H, 5.84; N, 6.27%. Found: C, 80.59; H, 5.84; N, 6.11%

(13-d)

Synthesis of (4R)-4-hydroxy-2-[4-(4-methoxyphenyl)phenyl]decanenitrile:

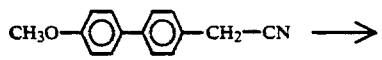

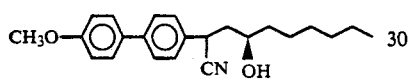

To a solution of 1.02 g (4.6 mmol) of 4-(4-methoxyphenyl)phenylacetonitrile in 40 ml of tetrahydrofuran (THF) was added, at −78° C., 1.5 M n-BuLi solution in hexane in an amount of 3.6 ml (5.5 mmol). This mixture was stirred for 1 hour. Thereto were added a solution of 705 mg (5.5 mmol) of (R)-1,2-epoxyoctane in 20 ml of THF and 5 ml of HMPA. The resulting mixture was warmed to room temperature, and then stirred overnight. The reaction mixture was neutralized with 3 M hydrochloric acid, and then subjected to extraction with 300 ml of ethyl acetate. The resulting ethyl acetate solution was washed with saturated sodium chloride aqueous solution, dried with anhydrous magnesium sulfate, filtered, and then concentrated. The residue was separated and purified by column chromatography (hexane/ethyl acetate=3/1), thereby obtaining 1.05 g (yield 65%) of (4R)-4-hydroxy-2-[4-(4-methoxyphenyl)phenyl]decanenitrile.

Colorless crystals

IR (KBr) 3450, 2950, 2240, 1610, 1500, 1250, 1100, 1040, 820 cm$^{-1}$ $^1$H NMR (CDCl$_3$) δ 0.86 (t, J=7.2 Hz) and 0.89 (t, J=6.7 Hz) total 3H, 1.22–1.39 (m, 8H), 1.42–1.47 (m, 2H), 2.01 (ddd, J=13.8, 9.7, 3.2 Hz) and 1.86 (ddd, J=13.9, 10.6, 4.4 Hz) total 1H, 2.14 (ddd, J=13.9, 9.7, 5.5 Hz) and 2.04 (ddd, J=13.9, 10.6, 2.4 Hz) total 1H, 3.85 (s, 3H), 3.46 (ddt, J=9.7, 6.4, 3.3 Hz) and 3.99 (ddt, J=10.4, 6.4, 3.4 Hz) total 1H, 4.10 (dd, J=9.6, 5.5 Hz) and 4.21 (dd, J=11.5, 4.4 Hz) total 1H, 6.98 (d, J=8.8 Hz, 2H), 7.40 (d, J=8.2 Hz, 2H), 7.51 (d, J=8.9 Hz, 2H), 7.56 (d, J=8.4 Hz, 2H).

MS m/z: 351 (M$^+$, 27), 333 (24), 248 (11), 236 (18), 235 (100), 223 (18), 222 (40), 179 (16)

(13-e)

Synthesis of (4R)-4-p-toluenesulfonyloxy-2-[4-(4-methoxyphenyl)phenyl]decanenitrile:

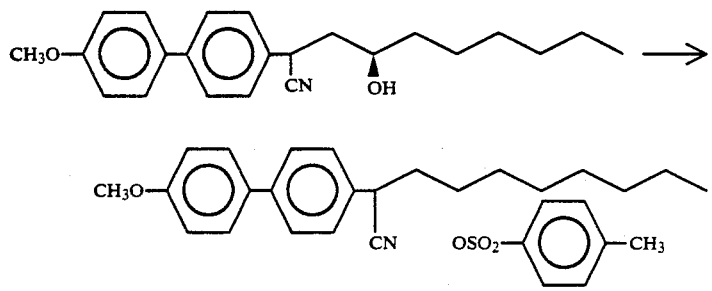

To a solution of 186 mg (0.53 mmol) of (4R)-4-hydroxy-2-[4-(4-methoxyphenyl)phenyl]decanenitrile in 10 ml of pyridine were added a solution of 303 mg (1.6 mmol) of p-toluenesulfonyl chloride in 20 ml of pyridine and 10 mg of DMAP. The resulting mixture was stirred at room temperature overnight. The pyridine was then removed by evaporation under reduced pressure. The residue was separated and purified by column chromatography (hexane/ethyl acetate=4/1), thereby obtaining 130 mg (yield 49%) of (4R)-4-p-toluenesulfonyloxy-2-[4-(4-methoxyphenyl)phenyl]decanenitrile.

Colorless viscous oil

IR (neat) 3050, 2950, 2875, 2250, 1740, 1610, 1505, 1465, 1370, 1250, 1175, 1100, 1040, 900, 820 cm$^{-1}$ $^1$H NMR (CDCl$_3$) δ 0.83 (t, J=7.3 Hz) and 0.85 (t, J=6.9 Hz) total 3H, 1.09–1.24 (m, 8H), 1.58–1.67 (m, 2H), 2.11–2.20 (m) and 2.38–2.49 (m) total 2H, 2.45 (s) and 2.46 (s) total 3H, 3.85 (s) and 3.86 (s) total 3H, 3.85–3.89 (m) and 3.95 (dd, J=8.2 and 6.6 Hz) total 1H, 4.55 (m) and 4.76 (m) total 1H, 6.98 (d. J=8.8 Hz) and 6.99 (d, J=8.8 Hz) total 2H, 7.30–7.39 (m, 4H), 7.49–7.57 (m, 3H), 7.80 (d, J=8.3 Hz) and 7.87 (d, J=8.4 Hz) total 2H MS m/z: 505 (M$^+$, 1.0), 333 (57), 235 (53), 222 (100), 179 (18)

(13-f)

Synthesis of (1R,2S)-1-cyano-2-hexyl-1-[4-(4-methoxyphenyl)cyclopropane:

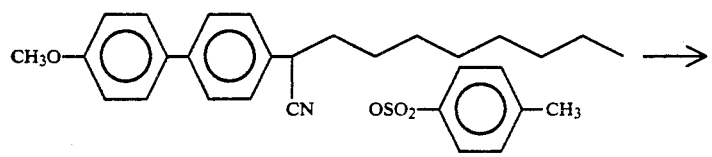

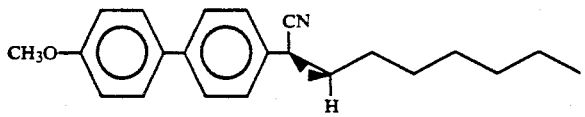

To a mixture of 107 mg (2.8 mmol) of sodium hydride (60%, in oil) with 10 ml of DMF was added, with cooling with ice, a solution of 1.13 g (2.2 mmol) of (4R)-4-toluenesulfonyloxy-2-[4-(4-methoxyphenyl)phenyl]-decanenitrile in 10 ml of DMF. This mixture was stirred at room temperature for 1 hour, neutralized with 3 M hydrochloric acid, and then subjected to extraction with 250 ml of ethyl acetate. The resulting ethyl acetate solution was concentrated under reduced pressure. The residue was separated by column chromatography (hexane/ethyl acetate=10/1), and then further separated and purified by high-pressure liquid chromatography for separation (Tosoh Corporation, Silica gel-60, 21.5 mmD×300 mm, hexane/ethyl acetate=20/1). Thus, 641 mg (yield 86%) of a nonpolar product, (1R,2S)-1-cyano- 2- hexyl -1-[4-(4methoxyphenyl)phenyl]cyclopropane, and 66 mg (yield 9%) of a polar product, (1S,2S)-1-cyano-2-hexyl-1-[4-(4methoxyphenyl)-phenyl]-cyclopropane, were obtained.

Identification data for the nonpolar product, (1R,2S)-1-cyano-2-hexyl-1-[4-(4-methoxyphenyl)phenyl]-cyclopropane are as follows.

Colorless plates, Melting point 101°-102° C.
$[\alpha]_D^{20}$ +50.8° (C=1.07, CDCl$_3$)
IR (KBr) 2960, 2920, 2850, 2230, 1600, 1500, 1440, 1290, 1250, 1035, 820, 800 cm$^{-1}$
$^1$H NMR (CDCl$_3$) δ 0.89 (t, J=6.9 Hz, 3H), 1.30-1.42 (m, 6H), 1.43 (dd, J=7.0, 4.9 Hz, 1H), 1.51-1.61 (m, 3H), 1.62 (dd, J=8.4, 4.9 Hz, 1H, 1.70-1.77 (m, 2H), 3.84 (s, 3H), 6.70 (d, J=8.8 Hz, 2H), 7.31 (d, J=8.4 Hz, 2H), 7.50 (d, J=8.8 Hz, 2H, 7.51 (d, J=8.4 Hz, 2H)
MS m/z: 333 (M$^+$, 32), 236 (19), 235 (100), 220 (10) 192 (11)
Elementary analysis: Calculated for C$_{23}$H$_{27}$NO: C, 82.84; H, 8.16; N, 4.20%. Found: C, 82.92; H, 8.26; N, 4.06%

(13-g)

Synthesis of (1R,2S)-1-cyano-2-hexyl-1-[4-(4-hydroxyphenyl)phenyl]cyclopropane:

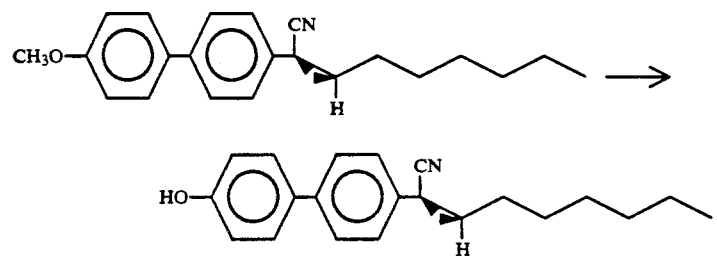

To a solution of 562 mg (4.2 mmol) of aluminum chloride and 3 ml of dimethyl sulfide in 20 ml of dichloromethane was added, at 0° C, a solution of 468 mg (1.4 mmol) of (1R,2S)-1-cyano-2-hexyl-1-[4-(4methoxyphenyl)phenyl]cyclopropane in 10 ml of dichloromethane. This mixture was heated to reflux for 30 minutes. The resulting reaction mixture was neutralized with saturated sodium hydrogen carbonate aqueous solution, filtered through Celite, and then subjected to extraction with 250 ml of ether. The resulting ether solution was subjected to separation and purification by column chromatography (hexane/ethyl acetate=3/1), thereby obtaining 358 mg (yield 79%) of (1R,2S)-1-cyano-2-hexyl-1-[4-(4-hydroxyphenyl)cyclopropane.

Colorless prisms, Melting point 114°-115° C.
$[\alpha]_D^{20}$ +52.8° (c=0.91, CHCl$_3$)
IR (KBr)3420, 2970, 2940, 2860, 2240, 1680, 1520, 1270, 1220, 1175, 830, 805 cm$^{-1}$
$^1$H NMR (CDCl$_3$) δ 0.89 (t, J=6.9 Hz, 3H), 1.28-1.42 (m, 6H), 1.43 (dd, J=7.0, 5.0 Hz, 1H), 1.50-1.61 (m, 1H), 1.62 (dd, J=8.4, 4.9 Hz, 1H), 1.68-1.79 (m, 2H), 6.99 (d, J=8.7 Hz, 2H), 7.30 (d, J=8.5 Hz, 2H), 7.44 (d, J=8.7 Hz, 2H), 7.50 (d, J=8.5 Hz, 2H)
MS m/z: 319(M$^+$, 15), 222 (20), 221 (10)
Elementary analysis: Calculated for C$_{22}$H$_{25}$NO: C, 82.72; H, 7.89; N, 4.39%. Found: C, 82.77; H, 7.95; N, 4.38%

EXAMPLE 14

Synthesis of 4-((1R,2S)-1-cyano-2-hexylcyclopropyl)phenyl 4-(4-octyloxyphenyl)benzoate In 8 ml of dichloromethane were dissolved 66 mg of 4-(4-octyloxyphenyl)benzoyl chloride and 36 mg of (1R,2S)-1-cyano-2-hexyl-1-(4-hydroxyphenyl)cyclopropane as obtained in Example 11. Thereto was added 0.5 ml of pyridine. The resulting mixture was stirred for 8 hours with refluxing, and then cooled. Thereafter, 50 ml of ether was added to the reaction mixture, and the resulting mixture was washed with diluted hydrochloric acid, water, and saturated sodium chloride aqueous solution, and then dried over anhydrous sodium sulfate. The solvent was removed by evaporation, and the residue was separated and purified by silica gel column chromatography (solvent: hexane/ethyl acetate=5/1). Thus, 30 mg of the desired compound was obtained as colorless crystals.

Identification data are given below.

$^1$H NMR (CDCl$_3$): δ 0.85-0.95 (m, 6H), 1.23-1.87 (m, 25H), 4.02(t, J=6.5 Hz, 2H), 7.00 (d, J=9 Hz, 2H), 7.21 (d, J=9 Hz, 2H), 7.34 (d, J=9 Hz, 2H), 7.59 (d, J=9 Hz, 2H), 7.69 (d, J=9 Hz, 2H), 8.22 (d, J=9 Hz, 2H)
IR (Nujol): 2250, 1730, 1600, 1520, 1275, 1195, 1180, 1080, 830, 760 cm$^{-1}$ The product obtained above was further purified by recrystallization it from ethanol, and the phase transition temperatures of the purified compound were measured. As a result, this compound showed an $S_A$ phase at temperatures below 136° C., and showed, at temperatures below 113.5° C., a chiral smectic phase which was not identified with respect to smectic structure. The melting point of the compound was 70° C.

EXAMPLE 15

Synthesis of
4-((1R,2S)-1-cyano-2-hexylcyclopropyl)-phenyl
4-octyloxybenzoate

The same procedures as in Example 14 were repeated except that 4-octyloxybenzoyl chloride was used in place of 4-(4-octyloxyphenyl)benzoyl chloride, thereby obtaining the desired compound as colorless crystals.

Identification data are given below.

$^1$H NMR (CDCl$_3$): δ 0.79–0.96 (m, 6H), 1.18–1.88 (m, 25H), 4.04 (t, J=6.5 Hz, 2H), 6.96 (d, J=7 Hz, 2H), 7.18 (d, J=7 Hz, 2H), 7.32 (d, J=7 Hz, 2H), 8.12 (d, J=7 Hz, 2H)

IR (Nujol): 2250, 1730, 1605, 1510, 1410, 1210, 1160, 840, 760 cm$^{-1}$

The phase transition temperatures of this compound are shown in Table 2.

EXAMPLE 16

Synthesis of
4-((1R,2S)-1-cyano-2-hexylcyclopropyl)-phenyl
4-[4-((R)-1-methylheptyloxy)phenyl]benzoate The same procedures as in Example 14 were repeated except that 4-[4-((R)-1-methylheptyloxy)-phenyl]benzoyl chloride was used in place of 4-(4-octyloxyphenyl)-benzoyl chloride, thereby obtaining the desired compound as colorless crystals.

Identification data are given below.

$^1$H NMR (CDCl$_3$): δ 0.80–0.92 (m, 6H), 1.20–1.82 (m, 26H), 4.33–4.38 (m, 1H), 6.90 (d, J=9 Hz, 2H), 7.02 (d, J=9 Hz, 2H), 7.21 (d, J=9 Hz, 2H), 7.49 (d, J=9 Hz, 2H), 7.68 (d, J=9 Hz, 2H), 8.22 (d, J=9 Hz, 2H)

EXAMPLE 17

Synthesis of
4-((1R,2S)-1-cyano-2-hexylcyclopropyl)-phenyl
4-(5-hexylpyrimidin-2-yl)benzoate The same procedures as in Example 14 were repeated except that 4-(5-hexylpyrimidin-2-yl)benzoyl chloride was used in place of 4-(4-octyloxyphenyl)-benzoyl chloride, thereby obtaining the desired compound as colorless crystals. Identification data are given below.

Identification data are given below.

$^1$H NMR (CDCl$_3$): δ 1.29–1.48 (m, 6H), 1.49–1.60 (m, 20H), 2.67 (t, J=5.5 Hz, 2H), 3.72 (m, 1H), 7.23 (d, J=7.5 Hz, 2H), 7.34 (d, J=7.5 Hz, 2H), 8.29 (d, J=9 Hz, 2H), 8.58 (d, J=9 Hz, 2H), 8.69 (s, 2H)

EXAMPLE 18

Synthesis of
4-((1S,2S)-1-cyano-2-hexylcyclopropyl)-phenyl
4-(4-octyloxyphenyl)benzoate The same procedures as in Example 14 were repeated except that (1S,2S)-1-cyano-2-hexyl-1-(4-hydroxyphenyl)cyclopropane as obtained in Example 12 was used as the raw compound, thereby obtaining the desired compound as colorless crystals.

Identification data are give below.

$^1$H NMR (CDCl$_3$): δ 0.72–1.91 (m, 31H), 4.02 (t, J=6 Hz, 2H), 7.00 (d, J=9 Hz, 2H), 7.25 (d, J=9 Hz, 2H), 7.41 (d, J=9 Hz, 2H), 7.59 (d, J=9 Hz, 2H), 7.69 (d, J=9 Hz, 2H), 8.22 (d, J=9 Hz, 2H)

EXAMPLE 19

Synthesis of
4-((1S,2S)-1-cyano-2-hexylcyclopropyl)-phenyl
4-octylbenzoate

The same procedures as in Example 18 were repeated except that 4-octylbenzoyl chloride was used in place of 4-(4-octyloxyphenyl)benzoyl chloride, thereby obtaining the desired compound as colorless crystals.

Identification data are given below.

$^1$H NMR (CDCl$_3$): δ 0.80–0.92 (m, 6H), 1.07–1.40 (m, 21H), 1.58–1.87 (m, 2.70 (t, J=8 Hz, 2H), 7.22 (d, J=9 Hz, 2H), 7.31 (d, J=9 Hz, 2H), 7.40 (d, J=9 Hz, 2H), 8.09 (d, J=9 Hz, 2H)

IR (Nujol): 2250, 1740, 1610, 1520, 1420, 1310, 1265, 1210, 1180, 1070, 1020, 880, cm$^{-1}$

EXAMPLE 20

Synthesis of
(1R,2S)-1-cyano-2-hexyl-1-[4-{4-(4-octyloxyphenyl)-phenylmethoxy}phenyl]cyclopropane In 10 ml of DMF was dissolved 49 mg of (1R,2S)-1-cyano-2-hexyl-1-(4-hydroxyphenyl)cyclopropane as obtained in Example 11. Thereto was added 34 mg of potassium t-butoxide, and the resulting mixture was stirred at room temperature for 70 minutes. Thereto was added dropwise a solution of 98 mg of 4-(4-octyloxyphenyl)benzyl bromide in 3 ml of DMF, and this mixture was stirred for 6 hours. Thereafter, 20 ml of 5% hydrochloric acid was added to the reaction mixture, and the resulting mixture was subjected to extraction with 50 ml of ether. The resulting organic layer was washed with water and then with saturated sodium chloride aqueous solution, and dried over anhydrous sodium sulfate. The solvent was removed by evaporation and the residue was purified by silica gel column chromatography (solvent: hexane/ethyl acetate=10/1), thereby obtaining 103 mg of the desired compound in the form of white crystals.

Identification data are given below.

$^1$H NMR (CDCl$_3$): δ 0.89 (t, J=7 Hz, 6H), 1.23–1.82 (m, 25H), 4.00 (t, J=6.5 Hz, 2H), 5.08 (s, 2H), 6.94–6.98 (m, 4H), 7.21 (d, J=9 Hz, 2H), 7.46 (d, J=9 Hz, 2H), 7.51 (d, J=9 Hz, 2H), 7.56 (d, J=9 Hz, 2H)

IR (Nujol): 2250, 1905, 1875, 1610, 1590, 1530, 1515, 1260, 1130, 1120, 1050, 815 cm$^{-1}$

EXAMPLE 21

Synthesis of
4-((1R,2S)-1-cyano-2-hexylcyclopropyl)phenyl
(S)-4-[4-(2-propoxypropanoyloxy)phenyl]benzoate
(Compound No. 8 in Table 2)

In 10 ml of dichloromethane were dissolved 83 mg of (S)-4-[4-(2-propoxypropanoyloxy)phenyl]benzoyl chloride and 65 mg of (1R,2S)-1-cyano-2-hexyl-1-(4-hydroxyphenyl)cyclopropane. To this solution was added 0.5 ml of pyridine. The resulting mixture was stirred for 3 hours under reflux. The reaction mixture was cooled, and then ether was added thereto. The ethanol phase was separated, washed with diluted hydrochloric acid, water, and then saturated sodium chloride aqueous solution, and dried over anhydrous sodium sulfate. The solvent was removed by evaporation and the residue was purified by silica gel column chromatography (solvent: hexane/ethyl acetate=5/1). Recrystallization from ethanol afforded, thereby obtaining 61 mg of the desired compound as colorless crystals.

NMR and IR data are given below.

$^1$H NMR (CDCl$_3$): δ 0.85-1.0 (m, 6H), 1.3-1.8 (m, 17H), 3.5 (m, 1H), 3.7 (m, 1H), 4.23 (q, 1H), 7.2-7.4 (m, 6H), 7.7 (m, 4H), 8.26 (d, 2H)

R (Nujol): 2250, 1765, 1730, 1610, 1520, 1280, 1220, 1190, 1130, 1080, 1010, 880, 770, 700 cm$^{-1}$ The phase transition temperatures of this compound were measured. As a result, it showed an S$_A$ phase at temperatures not higher than 46.5° C., and its melting point was 48.5° C.

EXAMPLE 22

Synthesis of 4-((1R,2S)-1-cyano-2-hexylcyclopropyl)phenyl (S)-4-(2-propoxypropanoyloxy)benzoate (Compound No. 9 in Table 2)

The same procedures as in Example 21 were repeated except that (S)-4-(2-propoxypropanoyloxy)-benzoyl chloride was used in place of (S)-4-[4-(2propoxypropanoyloxy)phenyl]benzoyl chloride, thereby obtaining the desired compound. This compound was oily at room temperature.

EXAMPLE 23

Synthesis of 4-[4-(1R,2S)-1-cyano-2-hexylcyclopropyl)-phenyl]phenyl trans-4-heptylcyclohexanecarboxylate In 10 ml of dichloromethane were dissolved 60 mg of trans-4-heptylcyclohexanecarbonyl chloride and 51 mg of ((1R,2S)-1-cyano-2-hexyl-1-[4-(4-hydroxyphenyl)-phenyl]cyclopropane as obtained in Example 13. To this solution was added 1.5 ml of pyridine. The resulting mixture was stirred for 6 hours under reflux, and then cooled. Thereafter, 50 ml of ether was added thereto, and the ethanol phase was washed with diluted hydrochloric acid, water, and then saturated sodium chloride aqueous solution, and dried over anhydrous sodium sulfate. The solvent was removed by evaporation and the residue was separated and purified by silica gel column chromatography (solvent: hexane/ethyl acetate=1/5), thereby obtaining 53 mg of the desired compound as colorless crystals.

IR (Nujol): 2250, 1755, 1605, 1500, 1320, 1210, 1170, 1160, 1130, 1010, 980, 930, 825, 560, 535 cm$^{-1}$ $^1$H NMR (CDCl$_3$): δ 0.87-1.00 (m, 6H), 1.23-2.16 (m, 34H), 2.49 (m, 1H), 7.13 (d, J=8.5 Hz, 2H), 7.33 (d, J=8.5 Hz, 2H), 7.5 (m, 4H)

The product obtained above was further purified by recrystallization from ethanol, and the phase transition temperatures of this purified compound were measured. As a result, the compound showed an S$_A$ phase below 103.5° C., and its melting point was 92.5° C.

EXAMPLE 24

Synthesis of 4-[4-((1R,2S)-1-cyano-2-hexylcyclopropyl)phenyl]phenyl (S)-4-(2-propoxypropanoyloxy)benzoate The same procedures as in Example 23 were repeated except that (S)-4-(2-propoxypropanoyloxy)-benzoyl chloride was used in place of trans-4-heptylcyclohexanecarbonyl chloride, thereby obtaining the desired compound. This compound did not crystallize even when left at a low temperature for a prolonged period of time and, hence, its melting point could not be measured. The compound, however, showed an S$_A$ phase at temperatures not higher than 39° C.

TABLE 2

| No. | Example | R$^1$ | $\left(A-Z\right)_m$ ring system | Y | C* | C** | R$^2$ | Phase transition temperature (°C.) |
|---|---|---|---|---|---|---|---|---|
| 1 | 14 | n-C$_8$H$_{17}$O | biphenyl | —COO— | (R) | (S) | n-C$_6$H$_{13}$ | 70 (Cr → Sx), 113.5 (Sx ⇌ S$_A$), 136 (S$_A$ ⇌ I) |
| 2 | 15 | n-C$_8$H$_{17}$O | phenyl | —COO— | (R) | (S) | n-C$_6$H$_{13}$ | 25 (Cr → I) |
| 3 | 16 | (R)-n-C$_6$H$_{13}$CH(CH$_3$)—O | biphenyl | —COO— | (R) | (S) | n-C$_6$H$_{13}$ | 130 (Cr → Sx), 151.5 (Sx ⇌ I) |
| 4 | 17 | n-C$_6$H$_{13}$ | pyridazine-phenyl | —COO— | (R) | (S) | n-C$_6$H$_{13}$ | 29.5 (Cr → Sx), 88 (Sx ⇌ I) |

TABLE 2-continued $$R^1-\left\{\phantom{\rule{0pt}{0pt}}\boxed{A}-Z\right\}_m-\boxed{\phantom{O}}-Y-\boxed{\phantom{O}}-\underset{CH_2}{\overset{CN}{\underset{|}{C}}}\overset{**}{\underset{}{CH}}-R^2$$

$$\left\{\phantom{\rule{0pt}{0pt}}\boxed{A}-Z\right\}_m-\boxed{\phantom{O}}-Y-$$

| No. | Example | $R^1$ | $\left\{\boxed{A}-Z\right\}_m-\boxed{\phantom{O}}-Y-$ | C* | C** | $R^2$ | Phase transition temperature (°C.) |
|---|---|---|---|---|---|---|---|
| 5 | 18 | n-$C_8H_{17}O$ | —⟨O⟩—⟨O⟩—COO— | (S) | (S) | n-$C_6H_{13}$ | 48 (Cr ⟶ Sx)<br>50 (Sx ⇌ I) |
| 6 | 19 | n-$C_8H_{17}$ | —⟨O⟩—COO— | (S) | (S) | n-$C_6H_{13}$ | oily substance |
| 7 | 20 | n-$C_8H_{17}O$ | —⟨O⟩—⟨O⟩—$CH_2O$— | (R) | (S) | n-$C_6H_{13}$ | 60.5 (Cr ⟶ Sx)<br>73.5 (Sx ⇌ Sc*)<br>96.5 (Sc* ⇌ $S_A$)<br>101 ($S_A$ ⇌ I) |
| 8 | 21 | (S)-n-$C_3H_7O$—CH(CH$_3$)—COO | —⟨O⟩—⟨O⟩—COO— | (R) | (S) | n-$C_6H_{13}$ | 48.5 (Cr ⟶ I)<br>46.5 (I ⟶ $S_A$) |
| 9 | 22 | (S)-n-$C_3H_7O$—CH(CH$_3$)—COO | —⟨O⟩—COO— | (R) | (S) | n-$C_6H_{13}$ | oily substance |
| 10 | 23 | n-$C_7H_{15}$ | —⟨H⟩—COO—⟨O⟩— | (R) | (S) | n-$C_6H_{13}$ | 92.5 (Cr ⟶ $S_A$)<br>103.5 ($S_A$ ⇌ I) |
| 11 | 24 | (S)-n-$C_3H_7O$—CH(CH$_3$)—COO | —⟨O⟩—COO—⟨O⟩— | (R) | (S) | n-$C_6H_{13}$ | 39 ($S_A$ ⇌ I) |

EXAMPLE 25

Preparation of Sc* liquid-crystal compositions

Base liquid crystal (A) consisting of the following ingredients was prepared.

$C_{10}H_{21}O$—⟨O⟩—⟨pyridine N⟩—$C_8H_{17}$    28%

$C_9H_{19}O$—⟨O⟩—⟨pyridine N⟩—$C_8H_{17}$    28%

$C_8H_{17}O$—⟨O⟩—⟨pyrazine N,N⟩—$C_8H_{17}$    24%

$C_8H_{17}O$—⟨O(F)⟩—⟨pyrimidine N,N⟩—⟨O⟩—$C_7H_{15}$    20%

This composition showed the following phase transition temperatures (°C.)

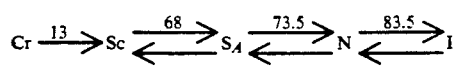

(N indicated a nematic phase.)

Base liquid crystal (B) consisting of the following ingredients was also prepared.

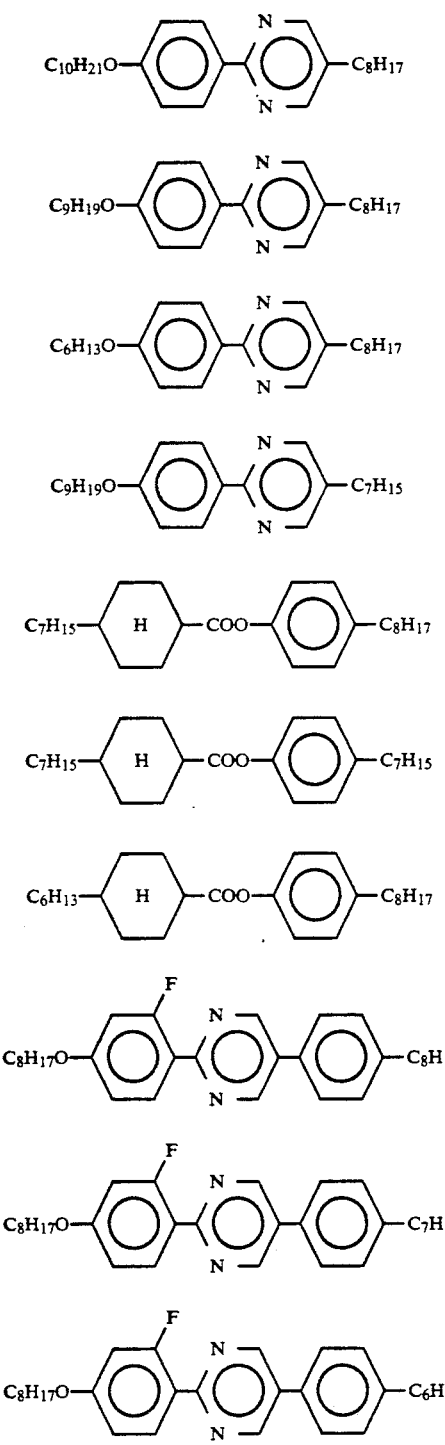

This composition showed the following phase transition temperatures (°C.).

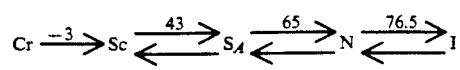

Further, base liquid crystal (C) consisting of the following ingredients was prepared.

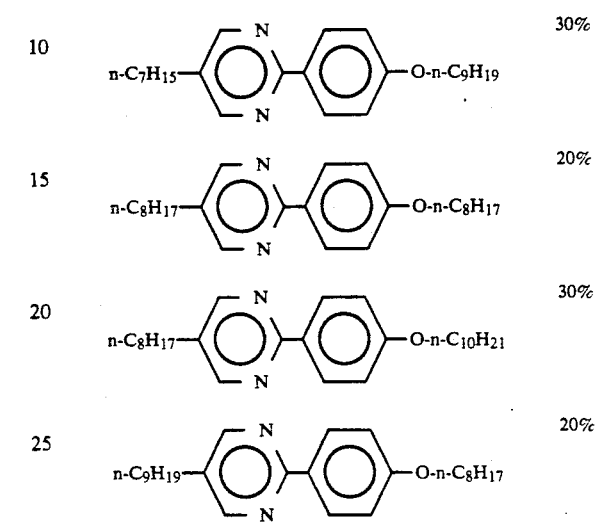

This composition showed the following phase transition temperatures (°C.).

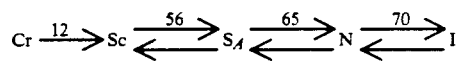

Furthermore, base liquid crystal (D) consisting of the following ingredients was prepared.

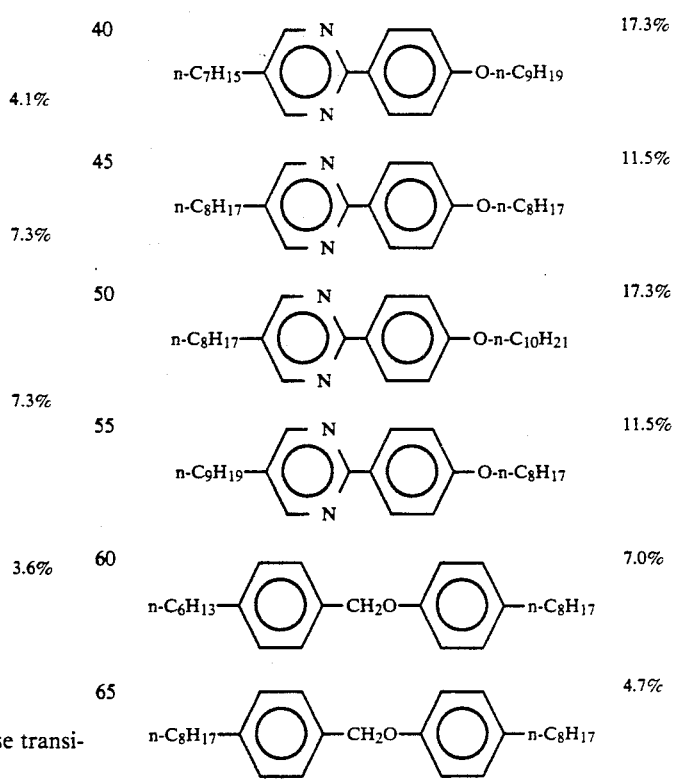

-continued

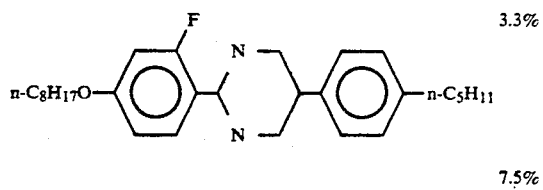   3.3%

7.5%

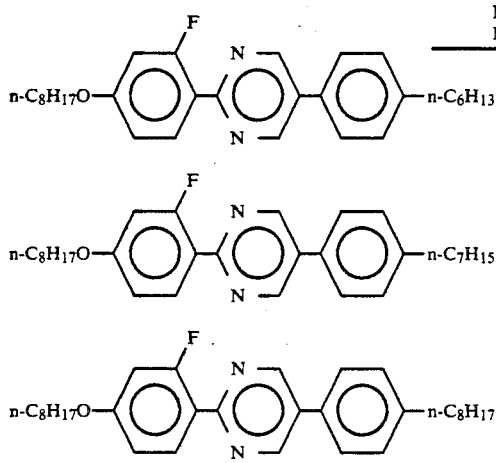

11.6%

8.3%

This composition showed the following phase transition temperatures (°C.), but its melting point could not be measured.

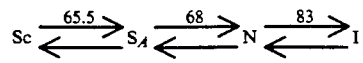

Thereafter, the compounds as obtained in Example 14 to 24 (Compounds Nos. 1 to 11 in Table 2) were added to the above-obtained base liquid crystals in amounts of 5 to 15%, thereby preparing Sc* liquid-crystal compositions. The phase transition temperatures of each of the thus-obtained compositions are shown in Table 3.

TABLE 3

Phase Transition Temperature of Sc* Liquid-Crystal Compositions

| Composition No. | Compound of General Formula (I) (No. in Table 2) and its Content | | Base Liquid Crystal | Phase Transition Temperature (°C.) | | | |
|---|---|---|---|---|---|---|---|
| M-1  | No. 1  | 5%  | (A) | Sc* 61.5 | $S_A$ 76   | N* 83   | I |
| M-2  | No. 1  | 10% | (A) | Sc* 57   | $S_A$ 82   | N* 84.5 | I |
| M-3  | No. 1  | 15% | (A) | Sc* 43.5 | $S_A$ 86.5 |         | I |
| M-4  | No. 1  | 5%  | (B) | Sc* 31   | $S_A$ 70   | N* 77.5 | I |
| M-5  | No. 2  | 5%  | (A) | Sc* 63   | $S_A$ 73   | N* 79.5 | I |
| M-6  | No. 2  | 10% | (A) | Sc* 56.5 | $S_A$ 71   | N* 76.5 | I |
| M-7  | No. 3  | 5%  | (A) | Sc* 71.5 | $S_A$ 74.5 | N* 83.5 | I |
| M-8  | No. 4  | 5%  | (A) | Sc* 64.5 | $S_A$ 74.5 | N* 84   | I |
| M-9  | No. 5  | 5%  | (A) | Sc* 65.5 | $S_A$ 75.5 | N* 82   | I |
| M-10 | No. 8  | 5%  | (B) | Sc* 45   | $S_A$ 68   | N* 74.5 | I |
| M-11 | No. 8  | 10% | (B) | Sc* 44.5 | $S_A$ 70   | N* 73   | I |
| M-12 | No. 10 | 10% | (C) | Sc* 47.5 | $S_A$ 70.5 | N* 71.5 | I |
| M-13 | No. 10 | 12% | (D) | Sc* 58   | $S_A$ 85   | N* 86   | I |
| M-14 | No. 10 | 15% | (C) | Sc* 42   | $S_A$ 73   |         | I |
| M-15 | No. 11 | 5%  | (C) | Sc* 57   | $S_A$ 65   | N* 68   | I |
| M-16 | No. 11 | 10% | (C) | Sc* 57.5 | $S_A$ 65   | N* 66   | I |

EXAMPLE 26

Preparation of display devices

Each Sc* composition obtained in Example 25 was heated to an isotropic liquid (I) phase. This composition was packed in a glass cell comprising two transparent electrode plates (aligned by polyimide-coating-and-rubbing treatment) about 2 μm apart, thereby preparing a thin film cell.

Each of the thus-prepared cells was gradually cooled to room temperature to obtain a cell in which the composition was in a uniformly oriented Sc* phase. In particular, the composition employing the compound of Example 21 and that employing the compound of Example 24 showed very large helical pitches in N* phase, and by gradually cooling the two cells to room temperature, monodomain cells were obtained in which the compositions were in uniformly oriented Sc* phase.

Square waves having an electric field intensity of 10 Vp-p/μm and a frequency of 50 Hz were applied to each of the above-obtained cells to measure its electro-optical response at 25° C. The results obtained are summarized in Table 4.

TABLE 4

Electro-Optic Response of Sc* Liquid-Crystal Compositions

| Composition No. | Electro-Optical Response (sec) | Spontaneous Polarization (nC/cm²) | Tilt Angele (degree) | Contrast | Helical Direction |
|---|---|---|---|---|---|
| M-1  | 134 | +3.3  | 26.9 | good | left |
| M-2  | 82  | +9.9  | 21.9 | good | left |
| M-3  | 62  | +11.4 | 17.7 | good | left |
| M-4  | 89  | +1.9  | 9.9  | good | left |
| M-5  | 79  | +7.4  | 25.5 | good | left |
| M-6  | 40  | +12.7 | 22.4 | good | left |
| M-8  | 211 | +1.4  | 25.9 | good | left |
| M-9  | 144 | -3.1  | 24.2 | good | left |
| M-10 | 36  | +8.8  | 18.6 | good | —*  |
| M-11 | 26  | +20.5 | 18.8 | good | —*  |

TABLE 4-continued

Electro-Optic Response of Sc* Liquid-Crystal Compositions

| Composition No. | Electro-Optical Response (sec) | Spontaneous Polarization (nC/cm$^2$) | Tilt Angele (degree) | Contrast | Helical Direction |
|---|---|---|---|---|---|
| M-12 | 76 | +13.4 | 25.4 | good | left |
| M-13 | 42 | +23.5 | 22.5 | good | left |
| M-14 | 26 | +14.2 | 11.9 | good | left |
| M-15 | 162 | +2.6 | 21.5 | good | right |
| M-16 | 54 | +14.8 | 22.4 | good | right |

*Unable to be determined because of very large helical pitch.

The optically active compound of general formula (I) according to the present invention shows a liquid-crystal phase and, when incorporated as chiral dopant into other Sc* liquid-crystal composition or Sc liquid-crystal composition, can induce a large spontaneous polarization to achieve high-speed response.

Furthermore, the optically active compound represented by general formula (I) and the intermediate therefor, both according to the present invention, can be easily produced industrially, and these compounds are colorless and chemically stable to light, water, heat, etc. Therefore, they are of good practical use.

The liquid-crystal material of this invention which comprises a chiral smectic liquid-crystal compound or composition can attain a high-speed response time as short as about 30 μsec and, hence, is extremely useful as a light-switching element for display.

While the invention has been described in detail and with reference to specific embodiments thereof, it will be apparent to one skilled in the art that various changes and modifications can be made therein without departing from the spirit and scope thereof.

What is claimed is:

1. An optically active compound represented by the following general formula (I):

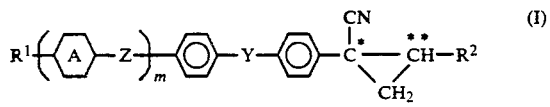

wherein R$^1$ represents an alkyl, alkoxyl, or alkoxyalkanoyloxy group which has 1 to 18 carbon atoms and may be substituted with fluorine, chlorine, or cyano group; R$^2$ represents an alkyl group having 1 to 18 carbon atoms;

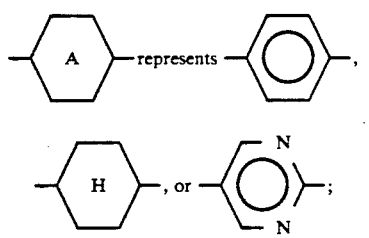

m is 0 or 1; Y represents a single bond, —CH$_2$O—, or —COO—; Z represents a single bond or —COO—; and C* and C** each independently represents an asymmetric carbon atom of the (R) or (S) configuration.

2. An optically active compound as claimed in claim 1, wherein

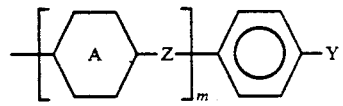

is selected from the group consisting of

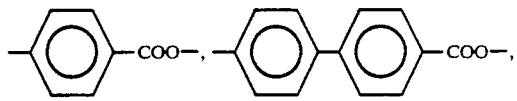

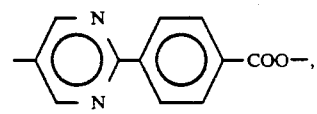

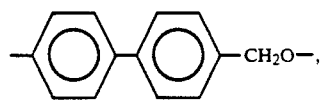

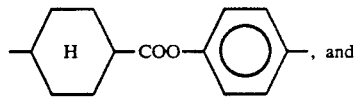

, and

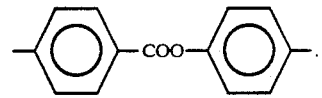

3. An optically active compound as claimed in claim 1, wherein m is 0 and Y is —COO—.

4. An optically active compound as claimed in claim 3, wherein R$^1$ is an optically active alkoxyalkanoyloxy group having 1 to 18 carbon atoms.

5. An optically active compound as claimed in claim 1, wherein m is 1.

6. An optically active compound as claimed in claim 5, wherein Y is —COO— and Z is a single bond.

7. An optically active compound as claimed in claim 6, wherein R$^1$ is selected from the group consisting of an optically active alkoxyl group having 1 to 18 carbon atoms and an optically active alkoxyalkanoyloxy group having 1 to 18 carbon atoms.

8. An optically active compound as claimed in claim 5, wherein Y is —CH$_2$O— and Z is a single bond.

9. An optically active compound as claimed in claim 5, wherein Y is a single bond and Z is —COO—.

10. An optically active compound as claimed in claim 9, wherein R$^1$ is an optically active alkoxyalkanoyloxy group having 1 to 18 carbon atoms.

11. A liquid crystal composition which contains an optically active compound as claimed in claim 1 and shows a ferroelectric chiral smectic phase.

* * * * *

UNITED STATES PATENT AND TRADEMARK OFFICE
CERTIFICATE OF CORRECTION

PATENT NO. : 5,064,564
DATED : November 12, 1991
INVENTOR(S) : Takehara et al

It is certified that error appears in the above-identified patent and that said Letters Patent is hereby corrected as shown below:

On the cover page, Item [75] "Sadao Takehara; Takeshi Kuriyama; Toru Fujisawa, Saitama; Kayoko Nakamura, Chiba; Tamejiro Hiyama; Kusumoto, Tetsuo, both of Kanagawa; Akiko Nakayama, Tokyo, all of Japan" should read --Sadao Takehara; Takeshi Kuriyama; and Masashi Osawa, all of Chiba; Toru Fujisawa, Saitama; Kayoko Nakamura, Chiba; Tamejiro Hiyama; Kusumoto, Tetsuo, both of Kanagawa; Akiko Nakayama, Tokyo, all of Japan--.

Signed and Sealed this

Thirtieth Day of March, 1993

Attest:

STEPHEN G. KUNIN

*Attesting Officer*   *Acting Commissioner of Patents and Trademarks*